United States Patent [19]

Newkirk

[11] Patent Number: 5,553,627
[45] Date of Patent: Sep. 10, 1996

[54] TONGUE DEPRESSOR

[76] Inventor: Darrel D. Newkirk, 2737 No. 102 St., Kansas City, Kans. 66109

[21] Appl. No.: 567,051

[22] Filed: Dec. 4, 1995

[51] Int. Cl.⁶ .................................................. A61C 5/14
[52] U.S. Cl. ........................ 128/860; 600/240; D24/136
[58] Field of Search .................................. 128/857, 858, 128/859, 860; 600/240, 241; D24/136

[56] References Cited

U.S. PATENT DOCUMENTS

| D. 319,503 | 8/1991 | Summers | D24/136 |
| D. 329,287 | 9/1992 | Ziese | D24/136 |
| D. 359,556 | 6/1995 | Hale | D24/136 |
| 2,425,945 | 8/1947 | Leach | 600/240 |

FOREIGN PATENT DOCUMENTS 1364134   5/1964   France .................................. 600/240

*Primary Examiner*—Michael A. Brown
*Attorney, Agent, or Firm*—Albert O. Cota

[57] ABSTRACT

An improved tongue depressor (10) that has a flat elongated blade (12) having a first end (14) and a second end (16). To the first end (14) is integrally attached a first tongue-contact section (34) and to the second end (16) is integrally attached a second tongue-contact section (70). Each of the tongue-contact sections has a lower surface (42) that includes sequentially, a downward slope (44), (80), a flat horizontal surface (48), (84) and an upper slope (52,88). The downward slope and the flat horizontal surface interface with the tongue and preferably have a non-slip surface (60). At the center and lower horizontal surface (20) of the elongated blade (12) is located a reinforcing protrusion (28) that prevents the tongue depressor from bending or breaking in the middle. Because the size of an adult mouth is generally larger than a child's mouth, one of the tongue-contact sections is made with a smaller width. Also, the tongue depressor is constructed of a plastic. Therefore, the aftertaste experienced by patients when using a wooden tongue depressor is eliminated.

21 Claims, 2 Drawing Sheets

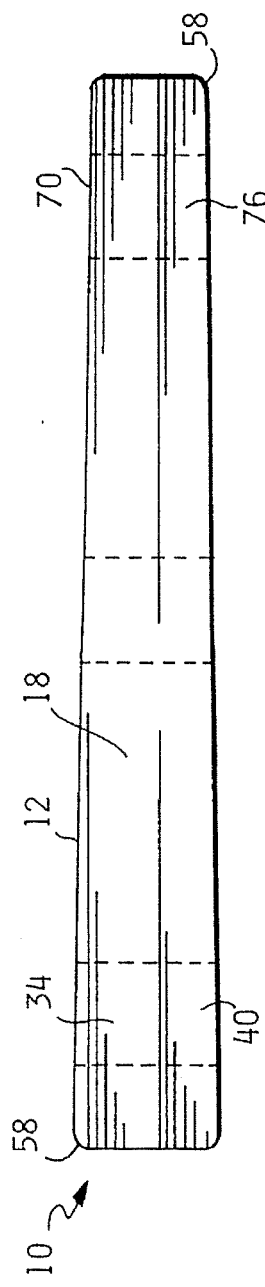
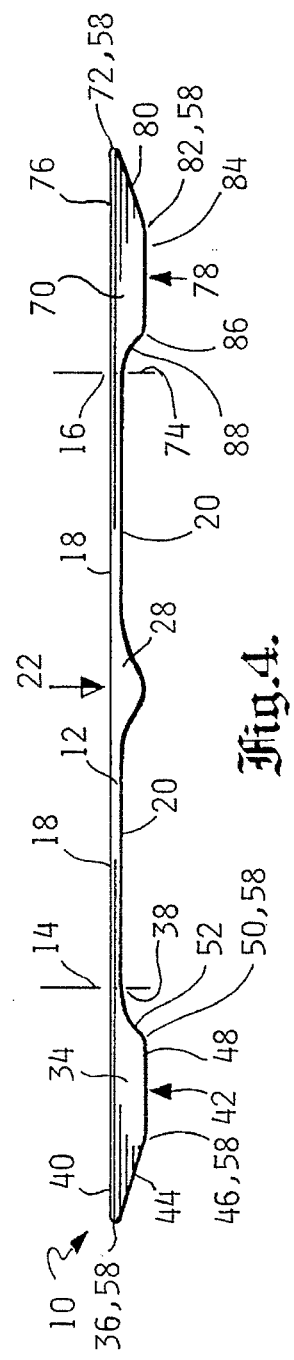
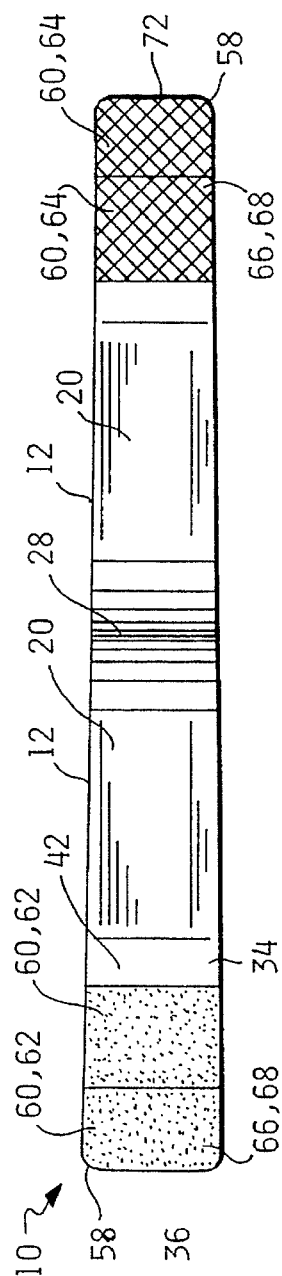

TONGUE DEPRESSOR

TECHNICAL FIELD

The invention pertains to the general field of medical instruments and more particularly to an improved tongue depressor designed to hold the tongue down during an examination of the mouth and surrounding areas.

BACKGROUND ART

It is often necessary for an individual to undergo an examination of the mouth or upper throat, to facilitate a doctor or dentist in determining the cause of a particular ailment. The most common instrument for this examination is a tongue depressor which is used in conjunction with a light or other viewing device. A tongue depressor permits the examining of the pharynx when the tongue is moved downward, by a pressure exerted thereon. Tongue depressors also allow the reaching of the frenum labii and the frenum linguae, so that it is possible to examine these parts and surrounding regions, such as the gums, the internal mucous membrane of the lips and the mucous membrane of the mouth.

A doctor, dentist, nurse or hospital attendant will usually insert a conventional wooden tongue depressor as shown in FIG. 1 into a patient's mouth for the duration of the examination. A disadvantage of this procedure, especially when performed by a person with little training, is that the tongue depressor can be improperly inserted and may provoke choking, damage to the mouth and surrounding tissue or blockage of the air passageway, resulting in possible suffocation. This is due to the limitations, imposed by current conventional wooden tongue depressor's inherent design. Furthermore, such conventional tongue depressors are frequently incapable of preventing tongue biting and have the danger of breaking and thus splintering within a patient's mouth.

An additional defect of wooden tongue depressors is that they do not possess a tongue-contact surface sufficient enough to hold the tongue down during examination. In addition, wooden tongue depressors with an insufficient tongue contact surface often slip off the wet tongue during the tongue depressing process. These problems are further exacerbated because no consideration has been given to the difference in sizes of mouths, particularly between the mouths of children and the mouths of adults. Also, because conventional tongue depressors are made of wood, there exists the problem of an unpleasant aftertaste, resulting from the tongue depressor being placed directly upon the tastebuds.

Accordingly, there is a need for an improved tongue depressor that retains all of the positive characteristics of conventional tongue depressors while adding features that improve the safety during use, as well as, taking into consideration the unique necessities of both the adult-sized mouth and the child-sized mouth. Additionally, there is a need for a tongue depressor which is manufactured from a material other than wood and that is better designed to more properly achieve the desired results from use of such an instrument.

A search of the prior art did not disclose any patents that read directly on the claims of the instant invention, however the following U.S. patents are considered related:

| U.S. PAT. NO. | INVENTOR | ISSUED |
|---|---|---|
| 4,589,848 | Inoue | 20 May 1986 |
| 4,041,937 | Diaz | 16 August 1977 |
| 3,863,627 | Bouffard | 4 February 1975 |
| Des. 329,287 | Ziese | 8 September 1992 |
| Des. 305,797 | Robinson | 30 January 1990 |

The 4,589,848 Inoue patent discloses a tongue press that can be switchably adapted to both an external and internal tongue press holder. The tongue press can be embodied in various types, such as the type covering the whole surface area of the tongue and the type covering one-half or one side of the tongue. The invention allows the selective use of any desired type of tongue press according to the patient and the purpose of use.

The 4,041,937 Diaz patent discloses a tongue blade having a pressure pad for firmly depressing and holding a patient's tongue. The blade includes an attachable bite guard for protecting the patient's teeth and for maintaining a clear air passageway through the patient's mouth. A depth guide prevents over-insertion of the blade, In a modified embodiment, the pressure pad is premoistened with an antiseptic solution.

The 3,863,627 Bouffard patent discloses a mouth exploring device comprising a handle and an exploring strip connected to the handle. The strip has two convex lateral edge portions which extend in the front part of the strip and define a substantially V-shaped notch having convex flanks so that the strip has a generally heart-shaped profile.

The Des. 329,287 Ziese patent discloses a curved tongue depressor.

The Des. 305,797 Robinson patent discloses a tongue depressor holder to which can be inserted a tongue depressor that is disclosed in two tip designs.

DISCLOSURE OF THE INVENTION

The improved tongue depressor is designed to better hold down the tongue during an examination of the mouth and throat. The depressor has a flat, elongated blade having a first end and a second end. To the first end is integrally attached a first tongue-contact section and to the second end is integrally attached a second tongue-contact section. Across the width of the blade at the lower horizontal surface is located a reinforcing protrusion. The protrusion prevents the depressor from bending or breaking in the middle.

Each of the tongue-contact sections has a front end and a rear end. From the front end extends a downward slope that is followed by a flat horizontal surface and subsequently by an upper slope that terminates at the rear end of the section. The only difference between the two tongue-contact sections is that one of the sections has a narrower width to accommodate a smaller-sized mouth.

The downward slope, which is typically at an angle of $20°\pm5°$, better reproduces the actual tongue depressing motion. The purpose of the downward slope is to provide a flat and even contact surface on the tongue when the examiner has to lift the held end of the tongue depressor about 20° to depress the tongue. The flat horizontal surface is likewise angled for applying a downward straight pressure. To prevent the tongue-interfacing surfaces from sliding off a wet tongue, they are made with a non-slip surface, which may consist of stippling or cross-hatching. The improved tongue depressor is made of a plastic material, therefore it does not leave a patient with an unpleasant aftertaste, as do current wooden tongue depressors.

The non-slip surfaces can include a flavoring that is applied by either dipping the ends into a container with a flavoring or by brushing the ends with a flavored liquid prior to usage.

In view of the above disclosure, the primary objective of the invention is to provide a tongue depressor that retains all of the positive characteristics of current conventional tongue depressors while adding additional features that improve the safety and use of the tongue depressor during use.

Another object of the present invention is to provide a tongue depressor that has a larger contact surface with the tongue. This larger surface prevents the tongue depressor from repeatedly slipping off a patient's tongue.

It is a further object of the invention to provide a tongue depressor that includes surfaces that are designed to be resilient against the wet surface of a tongue. This will assist in keeping the tongue depressor firmly placed while in use.

Yet another object of the invention is to provide a tongue depressor that is reinforced in the center. This is the point where the forces of the tongue depressing motion converge and is therefore the point where breakage is most likely to occur.

A still further object of the invention is to provide a tongue depressor that is manufactured from a material other than wood, preferably plastic. A plastic tongue depressor would eradicate any danger of the tongue depressor breaking and splintering in a patient's mouth. Also, the unpleasant aftertaste that is commonly experienced by a patient after the use of a wooden tongue depressor would no longer be a problem.

These and other objects are achieved by providing a tongue depressor that offers a larger contact surface with a platform on each end and surfaces that are resilient against the wet surface of a tongue. The tongue depressor would also be reinforced in the center to prevent accidental breakage, and would have ends that are sized to better accommodate the different sizes of patients' mouths. The tongue depressor would be made of a material other than wood, preferably plastic, and would therefore eradicate any danger from breakage, as well as the unpleasant aftertaste commonly experienced by patients after having been examined with a wooden tongue depressor.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 3 is a top plan view of the improved tongue depressor showing that the width of the first tongue-contact section is greater than that of the second tongue-contact section.

FIG. 4 is a side elevational view of the improved tongue depressor showing the angular configuration of the first and second tongue-contact sections and a centrally located reinforcing protrusion.

FIG. 5 is a bottom plan view of the improved tongue depressor showing the non-slip lower surfaces of the first and second tongue-contact sections.

BEST MODE FOR CARRYING OUT THE INVENTION

Figure 1:
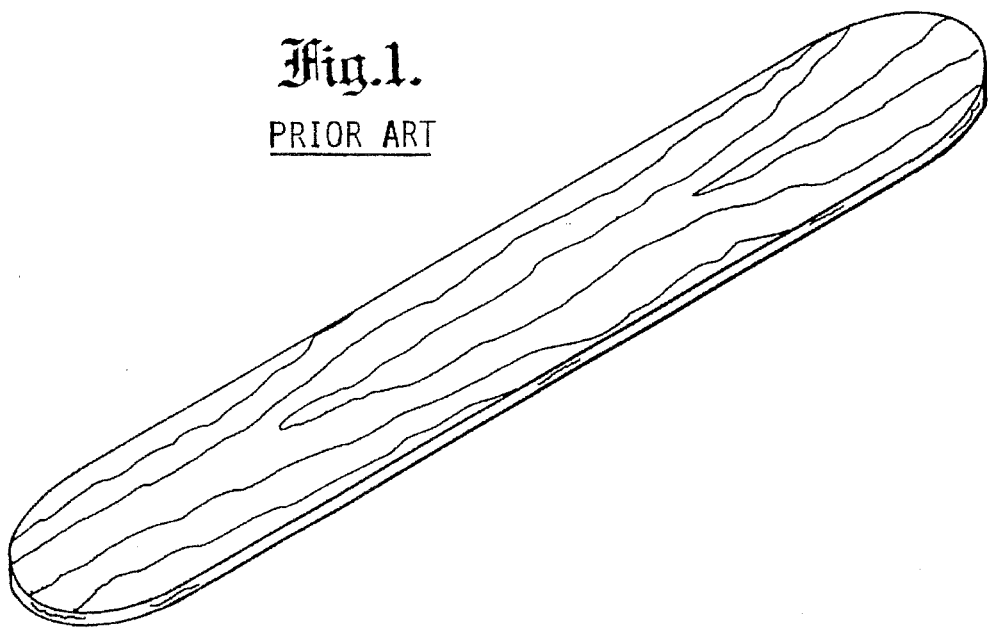
FIG. 1 is a perspective view of a conventional wooden tongue depressor.

The best mode for carrying out the improved tongue depressor 10 is presented in terms of a preferred embodiment that is shown in FIGS. 2–5. The tongue depressor 10 is comprised of a single integral unit that includes three integral major elements: a flat elongated blade 12, a first tongue-contact section 34 and a second tongue-contact section 70.

The flat elongated blade 12 as shown in FIGS. 2–5 has a first end 14, a second end 16, a substantially flat, upper horizontal surface 18 and a substantially flat, lower horizontal surface 20. Across the width of the tongue depressor 10 at the center 22 of the lower horizontal surface 20, is located an outward extending, reinforcing protrusion 28. The protrusion reinforces the middle of the tongue depressor 10 where all the forces of the tongue depressing motion converge. Thus, eliminating or at least minimizing the problem of the depressor bending or worse, breaking in the middle when excessive pressure is applied.

Figure 2:
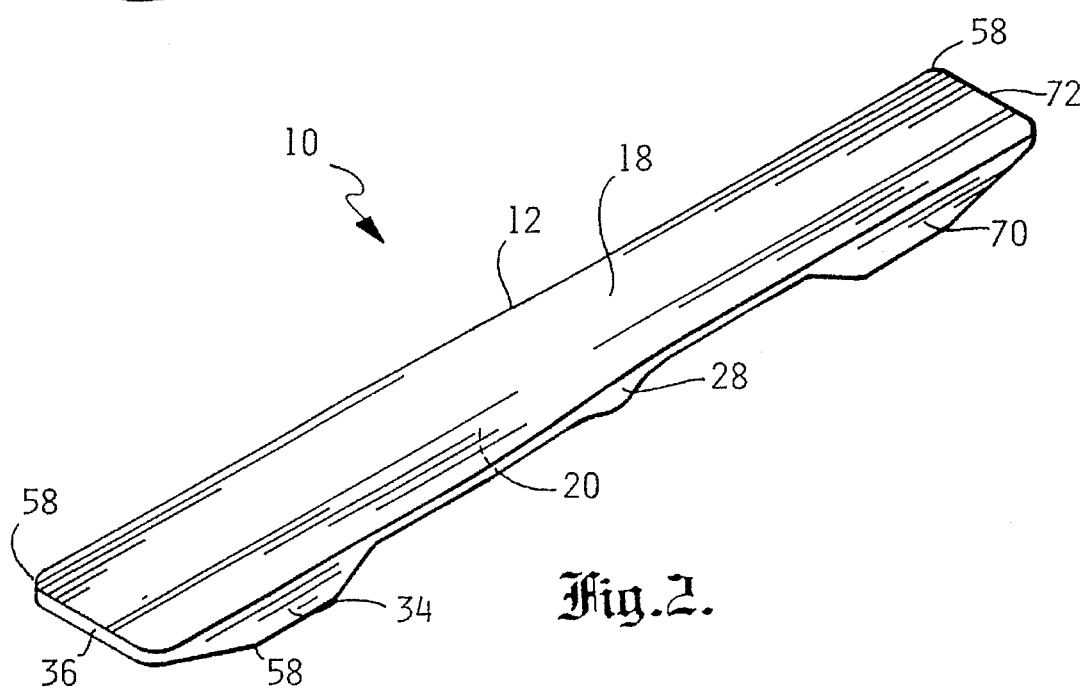
FIG. 2 is a perspective view of an improved tongue depressor that includes a first tongue-contact section and a second tongue-contact section.

The first tongue-contact section 34 is located on the left side of the tongue depressor 10 as shown in FIGS. 2 and 4. The section 34 has a front end 36, a rear end 38, a substantially flat, upper horizontal surface 40 that is flush with the upper horizontal surface 18 of the blade 12 and a lower surface 42 having a plurality of slopes. The rear end 38 as best shown in FIG. 4, is integrally attached to the first end 14 of the flat elongated blade 12. From the front end 36 extends inward, the lower surface 42 which includes, as shown in FIG. 4, a downward slope 44, that terminates at a front terminus 46. From the front terminus 46 extends a flat horizontal surface 48 that terminates at a rear terminus 50. From the rear terminus extends an upper slope 52 that terminates at the rear end The second tongue-contact section 70 is located on the right side of the tongue depressor 10 as shown in FIG. 5. This section also has a front end 72, a rear end 74, an upper horizontal surface 76 that is flush with the upper horizontal surface 18 of the blade 12, and a lower surface 78 having a plurality of slopes. The rear end 74 as best shown in FIG. 4, is integrally attached to the second end 16 of the flat elongated blade 12. From the front end 72 extends inward, the lower surface 78 which includes, as also shown in FIG. 4, a downward slope 80 that terminates at a front terminus 82. From the front terminus extends inward a flat horizontal surface 84 that terminates at a rear terminus 86 from where extends an upper slope 88 that terminates at the rear end 74.

The downward slope 44,80 of the first and second tongue-contact sections 34,70, when measured from the respective upper horizontal surface 40,76, can vary between 15° and 25° with a slope of 20° being preferred. The area of the downward slope 44,80 is used to keep contact with the tongue when applying a tongue depressing motion, while the area of the horizontal surface 48,84 is used to apply a downward straight pressure to the tongue.

Because the size of an adult's mouth is larger than that of a child, the width of the second tongue-contact section 70 is less than the width of the first tongue-contact section 34, as shown in FIGS. 3 and 5.

In the preferred embodiment, the width of the first section 34 is 0.8125 inches (2.06 cm) and the width of the second section is 0.6875 inches (1.75 cm). The maximum thickness of both sections is 0.1875 inches (0.48 cm). The above dimensions are preferred, however, they can vary by plus or minus 0.0625 inches (0.159 cm). The overall length of the tongue depressor can vary between 5.50 inches (13.97 cm) and 6.50 inches (16.50 cm), with a 6 inch (15.24 cm) depressor 10 preferred.

To prevent any sharp corner from injuring the mouth and the surrounding areas, all the corners 58 of the tongue depressor 10, as shown in FIGS. 2–5, are rounded. Also, to provide a positive tongue contact, the surface of the downward slopes 44,80 and the flat horizontal surfaces 48,84 of the first and second tongue contact sections 34,70 have a non-slip surface 60. The non-slip surface can consist as shown in FIG. 5 of a stippled surface 62 as shown on the first tongue-contact section 34 or a cross-hatched surface 64, as shown on the second tongue-contact section 70.

One of the problems inherent in conventional wooden tongue depressors is that they leave an unpleasant taste in the patient's mouth after a mouth/throat examination. To alleviate this problem, the non-slip surface 60 of the first and second tongue-contact sections 34,70 may include a flavoring 66 that is applied by an application means 68. The flavor application means 68 can consist of immersing the first and second tongue-contact sections 34,70 into a container containing a flavored liquid, i.e., cinnamon or by brushing the non-slip surface 60 with a flavor prior to inserting the depressor into a patient's mouth.

The tongue depressor 10 is injection molded of a recyclable material such as a high-impact plastic. A white plastic is preferred to convey cleanliness however, other light colors can also be used to enhance the utility of the depressor.

While the invention has been described in complete detail and pictorially shown in the accompanying drawings it is not to be limited to such details, since many changes and modifications may be made to the invention without departing from the spirit and the scope thereof. Hence, it is described to cover any and all modifications and forms which may come within the language and scope of the claims.

I claim:

1. An improved tongue depressor comprising:
   a) a flat elongated blade having a first end, a second end, a substantially flat, upper horizontal surface and a substantially flat, lower horizontal surface,
   b) a first tongue-contact section having a front end, a rear end, a substantially flat, upper horizontal surface, and a lower surface having a plurality of slopes, where the rear end is integrally attached to the first end of said blade, and
   c) a second tongue-contact section having a front end, a rear end, a substantially flat upper horizontal surface, and a lower surface having a plurality of slopes, where the rear end is integrally attached to the second end of said blade.

2. The tongue depressor as specified in claim 1 wherein the first tongue-contact section has a width greater than the width of the second tongue-contact section.

3. The tongue depressor as specified in claim 1 wherein the width of said first tongue-contact section is 0.8125 inches (2.06 cm), the width of said second tongue-contact section is 0.6875 inches (1.75 cm), and the maximum thickness of both sections is 0.1875 inches (0.48 cm), 4. The tongue depressor as specified in claim 1 wherein said depressor has an overall length of between 5.50 inches (13.97 cm) and 6.50 inches (16.51 cm).

5. The tongue depressor as specified in claim 1 wherein said blade further comprises a reinforcing protrusion that extends across the width and is located at the center of said blade.

6. The tongue depressor as specified in claim 5 wherein said reinforcing protrusion extends outward from the lower surface of said blade.

7. The tongue depressor as specified in claim 1 wherein from the front end of said first tongue-contact section extends a downward slope that terminates at a front terminus, from where extends inward a flat horizontal surface that terminates at a rear terminus, from where extends an upper slope that terminates at the rear end of said first tongue-contact section.

8. The tongue depressor as specified in claim 7 wherein the downward slope has a slope that is between 15° and 25° as measured downward from the flat upper horizontal surface.

9. The tongue depressor as specified in claim 8 wherein the surface of the downward slope and the flat horizontal surface of said first tongue-contact section further comprise non-slip surfaces.

10. The tongue depressor as specified in claim 9 wherein said non-slip surfaces of said first tongue-contact section comprises a stippled surface.

11. The tongue depressor as specified in claim 9 wherein said non-slip surfaces of said first tongue-contact section comprises a cross-hatched surface.

12. The tongue depressor as specified in claim 1 wherein from the front end of said second tongue-contact section extends a downward slope that terminates at a front terminus, from where extends inward a flat horizontal surface that terminates at a rear terminus, from where extends an upper slope that terminates at the rear end of said second tongue-contact section.

13. The tongue depressor as specified in claim 12 wherein the downward slope has a slope that is between 15° and 25° as measured downward from the flat upper horizontal surface.

14. The tongue depressor as specified in claim 13 wherein the surface of the downward slope and the flat horizontal surface of said second tongue-contact section further comprise non-slip surfaces.

15. The tongue depressor as specified in claim 14 wherein the non-slip surfaces of said second tongue-contact section comprises a stippled surface.

16. The tongue depressor as specified in claim 14 wherein the non-slip surfaces of said second tongue-contact section comprises a cross-hatched surface.

17. The tongue depressor as specified in claim 1 wherein the non-slip surface of said first and second tongue-contact sections further comprise a flavoring that is applied by an application means.

18. An improved tongue depressor comprising:
   a) a flat elongated blade having a first end, a second end, a substantially flat, upper horizontal surface and a substantially flat, lower horizontal surface where across the width at the center of the lower horizontal surface is located an outward extending reinforcing protrusion,
   b) a first tongue-contact section having a front end, a rear end and a substantially flat, upper horizontal surface, wherein the rear end is integrally attached to the first end of said blade and where from the front end extends a downward slope having a non-slip surface and that terminates at a front terminus, from where extends inward a flat horizontal surface having a non-slip surface that terminates at a rear terminus, from where extends an upper slope that terminates at the rear end of said first tongue-contact section, and c) a second tongue-contact section having a width that is less than the width of said first tongue-contact section, a front end, a Feat end and a substantially flat, upper horizontal surface, wherein the rear end is integrally attached to the second end of said blade and where from the front end extends a downward slope having a non-slip surface and that terminates at a front terminus, from where extends inward, a flat horizontal surface having a non-slip surface and that terminates at a rear terminus, from where extends an upper slope that terminates at the rear end of said second tongue-contact section.

19. The tongue depressor as specified in claim 18 wherein all the corners of said first and second tongue-contact section are rounded.

20. The tongue depressor as specified in claim 18 wherein the non-slip surface of said first and second tongue-contact sections further comprise a flavoring that is applied by an application means.

21. The tongue depressor as specified in claim 18 wherein the downward slope of said first and second tongue-contact sections is between 15° and 25° as measured from the flat upper horizontal surface.

\* \* \* \* \*